United States Patent
Chodorge et al.

(10) Patent No.: US 6,358,482 B1
(45) Date of Patent: *Mar. 19, 2002

(54) FACILITY FOR THE PRODUCTION OF ISOBUTENE AND PROPYLENE FROM HYDROCARBON CUTS CONTAINING FOUR CARBON ATOMS

(75) Inventors: Jean Alain Chodorge, Antony; Dominique Commereuc, Meudon; Jean Cosyns, Maule, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/520,241

(22) Filed: Mar. 7, 2000

Related U.S. Application Data

(62) Division of application No. 08/958,909, filed on Oct. 28, 1997, now Pat. No. 6,075,173.

(30) Foreign Application Priority Data

Oct. 28, 1996 (FR) .............................. 96 13298

(51) Int. Cl.⁷ .................................. B01J 8/02
(52) U.S. Cl. ................. 422/189; 422/131; 422/134; 422/190; 585/259; 585/518; 585/643; 585/647
(58) Field of Search .............. 422/188–190, 422/211, 131–134; 585/259–262, 277, 643, 644, 647

(56) References Cited

U.S. PATENT DOCUMENTS

| | | | | |
|---|---|---|---|---|
| 3,764,633 A | * | 10/1973 | Garner et al. | 208/143 |
| 5,120,894 A | | 6/1992 | McCauley | 585/664 |
| 5,449,852 A | * | 9/1995 | Chauvin et al. | 585/547 |
| 5,523,502 A | * | 6/1996 | Rubin et al. | 585/324 |
| 6,207,115 B1 | * | 3/2001 | Chodorge et al. | 422/134 |

FOREIGN PATENT DOCUMENTS

| | | |
|---|---|---|
| EP | 0 639 549 | 2/1995 |
| FR | 1493983 | 12/1967 |
| FR | 735727 | 10/1970 |

* cited by examiner

Primary Examiner—Hien Tran
(74) Attorney, Agent, or Firm—Millen, White, Zelano & Branigan, P.C.

(57) ABSTRACT

A facility for converting an olefinic $C_4$ cut to isobutene and propylene comprising, in succession:

1) a zone 1 for selective hydrogenation of olefins in the olefinic C4 cut with simultaneous isomerisation of butene-1 to butene-2, said zone comprising at least one device for introducing the olefinic C4 cut to be converted, at least one device for removing an effluent, and at least one device for introducing hydrogen, said zone also comprising at least one catalyst bed;

2) a separation zone, comprising at least one device for introducing the effluent from zone 1 directly connected to said at least one device for removing an effluent, at least one device for removing a first fraction comprising isobutene and butene-1, and at least one device for removing a second fraction comprising butene-2 and n-butane, wherein the second fraction comprises at most 1% by weight of isobutene and at most 1% by weight of butene-1;

3) a metathesis zone for metathesis of butene-2 with ethylene to produce propylene, wherein the metathesis zone comprises at least one device for introducing butene-2 from the second fraction of the separation zone, at least one device for introducing ethylene, and at least one device for removing propylene, and at least one catalyst comprising at least one rhenium oxide deposited on a support.

5 Claims, 1 Drawing Sheet

FACILITY FOR THE PRODUCTION OF ISOBUTENE AND PROPYLENE FROM HYDROCARBON CUTS CONTAINING FOUR CARBON ATOMS

CROSS REFERENCE TO RELATED APPLICATION

This application is a divisional application of application Ser. No. 08/958,909 filed Oct. 28, 1997, now U.S. Pat. No. 6,075,173 issued Jun. 13, 2000.

This application is also related to commonly assigned application Ser. No. 08/644,159 filed May 10, 1996, now U.S. Pat. No. 5,877,365, issued Mar. 2, 1999, by Chodorge, Commereuc, Cosyns, Duee, and Torck, said related application being incorporated by reference herein.

The invention concerns a facility for the production of isobutene and propylene from a $C_4$ cut.

Steam cracking feeds constituted by light paraffinic cuts produces ethylene and propylene which are required for petrochemistry. It also produces a certain number of other heavier products, in particular a $C_4$ hydrocarbon cut which principally contains 1,3-butadiene, isobutene, n-butenes and butanes, accompanied by traces of acetylenic hydrocarbons.

In addition to gasoline and gas oil as the principal products, catalytic cracking of heavy hydrocarbon feeds produces lighter products, among them a $C_4$ hydrocarbon cut which contains principally isobutane, isobutene, n-butenes and butanes, accompanied by small quantities of 1,3-butadiene and acetylenic hydrocarbons.

Until recently, only 1,3-butadiene and isobutene were of use in the polymer industry, in particular the tire industry for the former. An increase in the longevity of tires and a relative stagnation in demand have meant that there is now a surplus of butadiene which is not used or is not used properly. In contrast, there has been a reawakening in interest in isobutene which can be used, for example, for the synthesis of ethers for use as additives in automobile fuels or as a monomer for the synthesis of polyisobutene.

The present invention proposes a facility for the treatment of a $C_4$ hydrocarbon cut containing principally isobutene, n-butenes, butanes, and 1,3-butadiene in various quantities, which includes separating the isobutene by distillation and which can transform the 1,3-butadiene and n-butenes to propylene which can, for example, be used for polymerisation.

The relative proportions of ethylene and propylene produced in a steam cracking operation can be modulated to a certain extent by changing the nature of the feed and modifying the operating conditions (severity) of cracking. However, an operative mode which is oriented towards producing a larger proportion of propylene inevitably entrains a reduction in the ethylene yield and higher production of the $C_4$ cut and gasoline fraction.

A further aim of the present invention is to increase the production of propylene while maintaining a high yield of ethylene by treating the $C_4$ hydrocarbon cut and thus without the need for a reduction in the severity of the steam cracker.

In Applicants' issued patent application, now U.S. Pat. No. 6,075,173 issued Jun. 13, 2000, the process aspect of the invention was elected for the conversion of an olefinic $C_4$ cut to isobutene and propylene, the cut containing diolefins, butene-1, butene-2, isobutene and acetylenic impurities, the process comprising the following successive steps:

1) selective hydrogenation of diolefins and acetylenic impurities with isomerisation of butene-1 to butene-2 to obtain an effluent containing mainly butene-2 and isobutene, and containing practically no diolefins or acetylenic compounds, preferably by passing the cut in a liquid phase over a catalyst comprising at least one metal selected from the group formed by nickel, palladium and platinum, deposited on a support, at a temperature of 20–200° C., a pressure of 0.1–5 MPa, a space velocity of 0.5–10 $h^{-1}$, and with an $H_2$/diolefin (molar) ratio of 0.5 to 5, preferably 1 to 3;

2) separating, by distillation, an overhead cut containing mainly isobutene and butene-1 which was not converted during the first step, and a bottom cut containing essentially butene-2 and butane, at most 1% by weight of isobutene and at most 1% by weight of butene-1;

3) carrying out metathesis of the butene-2 cut from the preceding step with ethylene, in the presence of a catalyst comprising at least one rhenium oxide deposited on a support, at a temperature in the range 0° C. to 100° C., and at a pressure which is at least equal to the vapour tension of the reaction mixture at the reaction temperature, to obtain an effluent containing propylene, metathesis being followed by separation of the propylene.

BRIEF DESCRIPTION OF THE DRAWING

The process of the invention will now be described in more detail using the scheme shown in FIG. 1 using a $C_4$ hydrocarbon cut entering via a line 1, which contains principally isobutene, n-butenes, butanes, also varying amounts of butadiene. The $C_4$ cut is subjected to a succession of treatments carried out in the following steps, to produce isobutene and propylene:

selective hydrogenation of acetylenic hydrocarbons and butadiene with isomerisation of butene-1 to butene-2;

Figure 1:
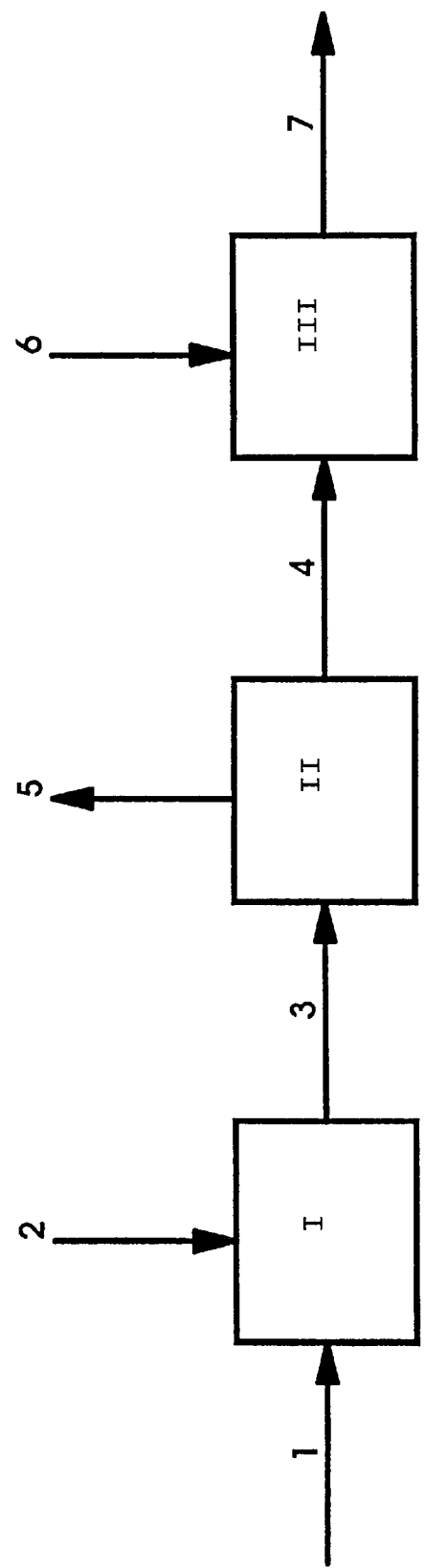

separation of the isobutene and butene-1 from the butene-2;

metathesis of butene-2 in the presence of ethylene (ethenolysis) producing propylene.

The succession of treatments in the process of the invention has a number of advantages. The most reactive compounds in the cut, namely 1,3-butadiene, for example, which is in varying amounts, also traces of acetylenic hydrocarbons, are transformed in the first step, and will thus not cause side reactions in the following steps. Further, selective hydrogenation of the diolefins (1,3-butadiene and 1,2-butadiene) to butenes and hydroisomerisation of butene-1 can considerably increase the concentration of butene-2 in the cut, which results in an even higher yield of propylene in the metathesis step.

Fractionation of the cut from the hydroisomerisation step, to isobutene and butene-1 and to butene-2, allows the isobutene to be upgraded in various ways without introducing pollutants into the fraction containing the butene-2 which then undergoes metathesis. It also means that a metathesis catalyst with a low or practically zero isomerising action can be used. Further, if, for example, isobutene is transformed into methyl-tertiobutylether by reaction with methanol, the butene-2 will not be contaminated by oxygen-containing by-products as is normal when this reaction is carried out directly on the hydroisomerised cut. The same is true when isobutene is transformed by polymerisation, a preferred route to upgrading isobutene.

Further, in the subsequent metathesis step, the low butene-1 content in the fraction which is rich in butene-2 can produce a propylene selectivity of close to 100%. Butene-1 will react with butene-2 to produce propylene and pentenes and it will react with itself to produce hexenes. Pentenes and hexenes are low value by-products which must be removed in an expensive process. Thus the process can appreciably increase the propylene yield, and facilitates recycling of butene-2 to the metathesis reaction as there are few pentenes and hexenes to be eliminated.

The invention of the present application concerns a facility (shown in FIG. 1) for carrying out the process described above and which comprises, in succession:

a zone I for selective hydrogenation with isomerisation of butene-1 to butene-2, said zone comprising at least one means 1 for introducing a cut to be converted, at least one means 3 for removing effluent and at least one means 2 for introducing hydrogen, said zone also comprising at least one bed of a catalyst which preferably comprises at least one metal selected from the group formed by nickel, palladium and platinum, deposited on a support;

a separation zone II, comprising at least one means 3 for introducing effluent from zone I, at least one means 5 for removing isobutene and butene-1, and at least one means 4 for removing butene-2 and n-butane;

a metathesis zone III containing at least one catalyst, preferably based on a rhenium oxide deposited on a support, and comprising at least one means 4 for introducing effluent from zone II, at least one means 6 for introducing ethylene and at least one means 7 for removing propylene.

More particularly, the $C_4$ cut originates from an upstream steam cracking zone, the means for introducing the cut to be converted into zone I being connected to the steam cracking zone, and the means for introducing ethylene into zone III is connected to the steam cracking zone.

The invention will now be described with reference to FIG. 1.

The principal aim of the first step is to transform butadiene and n-butenes to butene-2. The butene-2 is the source of the propylene which is produced in the last metathesis step in the presence of ethylene. It is thus desirable to maximise the yield of butene-2, i.e., to come as close as possible to the thermodynamic proportions. The second aim of this step is to eliminate traces of acetylenic hydrocarbons which are always present in these cuts and which poison or pollute the subsequent steps.

In the first step (zone I), the following reactions are carried out simultaneously in the presence of hydrogen supplied via line 2:

selective hydrogenation of butadiene to a mixture of n-butenes at thermodynamic equilibrium;

isomerisation of butene-1 to butene-2, to obtain a distribution which is close to thermodynamic equilibrium;

selective hydrogenation of the trace acetylenic hydrocarbons to butenes.

These reactions can be carried out using various specific catalysts comprising one or more metals, for example from group 10 of the periodic table (Ni, Pd, Pt), deposited on a support. A catalyst comprising at least one palladium compound fixed on a refractory mineral support, for example alumina, is preferably used. The quantity of palladium on the support can be in the range 0.01% to 5% by weight, preferably in the range 0.05% to 1% by weight. A variety of pre-treatment methods which are known to the skilled person can be applied to improve the selectivity for the hydrogenation of butadiene to butenes to the detriment of complete hydrogenation to butane which must be avoided. The catalyst preferably contains 0.05% to 10% by weight of sulphur. A catalyst constituted by palladium deposited on alumina, and with sulphur, is preferably used.

The catalyst can advantageously be carried out using the process described in French patent FR-93/09529, i.e., before charging it into the hydrogenation reactor, the catalyst is treated with at least one sulphur-containing compound diluted in a solvent, then the catalyst obtained containing 0.05% to 10% (by weight) of sulphur is charged into the reactor and activated in a neutral or reducing atmosphere at a temperature which is in the range 20° C. to 300° C., a pressure which is in the range 0.1 MPa to 5 MPa and a HSV which is in the range 50 $h^{-1}$ to 600 $h^{-1}$, and the feed is brought into contact with this activated catalyst.

The mode of using the catalyst, preferably a palladium catalyst, is not critical, but in general it is preferable to use at least one reactor in downflow mode passing through a fixed bed of catalyst. When the proportion of butadiene in the cut is high, as is the case, for example, with a steam cracking cut when butadiene is not to be extracted for specific uses, it may be of advantage to carry out the transformation in two reactors in series to better control the selectivity towards hydrogenation. The second reactor can be an upflow reactor and may act as a finishing reactor.

The quantity of hydrogen required for all of the reactions carried out in this step is adjusted as a function of the composition of the cut, so that advantageously the hydrogen is only in a slight excess with respect to the theoretical stoichiometry.

The operating conditions are selected so that the reactants and products are in the liquid phase. However, it may be advantageous to select an operating mode such that the products are partially vaporised at the reactor outlet, to facilitate thermal control of the reaction. The temperature can be between 20° C. and 200° C., preferably 50° C. to 150° C., more preferably 60° C. to 100° C. The pressure can be adjusted to between 0.1 MPa and 5 MPa, preferably between 0.5 MPa and 4 MPa and advantageously between 0.5 MPa and 3 MPa, so that the reactants are at least partly in the liquid phase. The space velocity can be in the range 0.5 $h^{-1}$ to 20 $h^{-1}$, preferably in the range 1 $h^{-1}$ to 10 $h^{-1}$, with an $H_2$/diolefins (molar) ratio of 0.5 to 5, preferably 1 to 3.

The hydroisomerisation reactor(s) can advantageously be followed by a stabilisation column which eliminates traces of gaseous hydrocarbons which may be present in the hydrogen supplied.

The aim of the second step (zone II) is to separate, by distillation, the $C_4$ cut from the preceding step, supplied via line a 3 to obtain a fraction containing isobutene and the majority of the butene-1, and a fraction containing a small quantity of butene-1, the butene-2 and n-butane. This now concentrated isobutene, recovered via line 5, can be used in various fashions. The butene-2 fraction is directed via a line 4 to the metathesis step.

The butene-2 fraction at the bottom of the distillation zone contains at most 1%, preferably at most 0.5% by weight of butene-1, and at most 1% and advantageously at most 0.5% by weight of isobutene. Further, the overhead loss of butene-2 is advantageously maintained at at most 3% by weight with respect to the butene-2 entering the column. An optimised distillation column operates with 90–120 plates and a reflux/feed ratio of 3–5.

The butene-2 fraction from the preceding step contains no external pollutant (for example oxygen-containing pollutants from an etherification step) and can thus be sent directly to a third step of the process (zone III). In this last step, butene-2 is reacted with ethylene supplied via a line 6, to give propylene by metathesis (leaving via a line 7). Because of the low quantity of butene-1 and isobutene in the feed, by-product formation is very low.

The metathesis of ethylene with butene-2 can be catalysed by a variety of metal oxides deposited on supports. A catalyst comprising at least one rhenium oxide deposited on a support composed of a refractory oxide containing at least alumina, and with an acid nature, is preferably used, for example alumina itself, silica-aluminas or zeolites.

Preferred examples are catalysts comprising rhenium heptoxide deposited on a gamma alumina analogous to that used in reforming catalysts, as described in U.S. Pat. No. 4,795,734. The rhenium content (expressed as rhenium metal) can be in the range 0.01% to 20%, preferably in the range 1% to 15% by weight. The catalysts undergo final thermal activation, for example at a temperature which is in the range 400° C. to 1000° C. for a period of 10 minutes to 5 hours in a non-reducing atmosphere.

Catalysts comprising rhenium heptoxide deposited on an alumina can also be modified by addition of an oxide of another metal. As an example, such modified catalysts comprise rhenium as an oxide, 0.01% to 20% by weight expressed as metallic rhenium, deposited on a support containing at least 75% by weight of alumina and 0.01% to 30% by weight of at least one oxide of a metal selected from the group formed by niobium and tantalum, as described in French patent FR-A-2 709 125.

The metathesis reaction is preferably carried out in the liquid phase, in the absence of oxygen, oxygen-containing compounds and moisture, and at a temperature which is in the range 0° C. to 200° C., preferably in the range 20° C. to 150° C., at a pressure which is at least equal to the vapour tension of the reaction mixture at the reaction temperature.

The catalyst can be used in a fixed bed. However, as it must be regenerated frequently, at least two reactors disposed in parallel must be used, one being in operation while the other is in regeneration mode. A moving catalytic bed is preferably used, such as that described in French patent FR-A-2 608 595. The catalyst is extracted at regular intervals from the bottom of the reactor and continuously transferred to a regeneration system from which it is returned to the top of the reactor.

Because of the limitations imposed by the thermodynamics, unconverted ethylene is fractionated in a first distillation column and recycled to the metathesis reactor. A second distillation column separates propylene and unconverted $C_4$ hydrocarbons which can be recycled to the metathesis reactor. The fractionation scheme is thus more simple than if a large quantity of butene-1 had been present in the feed, as it would have produced more pentenes and hexenes which would have had to have been eliminated before recycling the butenes.

When the process is applied to a $C_4$ steam cracking cut, it may be of advantage to integrate the metathesis unit with the cracker, to take advantage of the fractionation chain of the latter.

The following example illustrates the invention without limiting its scope.

EXAMPLE 1

A $C_4$ cut leaving a steam cracker had the composition shown in Table 1 (stream 1). Abbreviations used in the table are: MAPD=methylacetylene+propadiene, BBV=1,2-butadiene+1-butyne+vinylacetylene.

This $C_4$ cut first underwent hydrogenation and hydroisomerisation. It was continuously introduced, with the mass flow rate shown in Table 1 and at a pressure of 2 MPa, into a first reactor comprising a fixed bed of 2.6 T of a catalyst constituted by palladium on alumina which had first been sulphurised. Hydrogen (mixed with methane) was also injected into this reactor, as shown in Table 1 (stream 2). The effluent from this first reactor was then treated in a finishing reactor charged with 2.5 T of the same catalyst. At the outlet (Table 1, stream 3), the cut was free of acetylenic compounds and the butadiene had essentially been transformed into butenes, which were mainly butene-2s, the butene-1 having been isomerised. The cut was then treated in a stabilisation column where residual hydrogen and methane were separated. After this treatment, the cut had the composition of stream 4 (Table 1).

TABLE 1

| Stream n° (Example 1) (kg/h) | 1 $C_4$ feed | 2 Feed Hydro-isomerisation | 3 Outlet Hydro-isomerisation | 4 $C_4$ outlet Stabilisation | 5 Column head Isobutene | 6 Column bottom Isobutene | 7 Inlet Metathesis | 8 Outlet Metathesis |
|---|---|---|---|---|---|---|---|---|
| (C3 + C3 =) | 10 | 10 | 41 | | | | | |
| MAPD | 31 | 31 | | | | | | |
| Isobutane | 446 | 446 | 446 | 434 | 434 | | | |
| n-Butane | 545 | 545 | 988 | 981 | | 981 | 981 | 981 |
| Isobutene | 5741 | 5741 | 5741 | 5667 | 5575 | 92 | 92 | 46 |
| butene-1 | 3407 | 3407 | 1003 | 951 | 911 | 40 | 40 | 20 |
| Butene-2s | 2250 | 2250 | 12737 | 12686 | 386 | 12300 | 12300 | 1230 |
| 1,3-Butadiene | 8095 | 8095 | | | | | | |
| BBV | 104 | 104 | | | | | | |
| Hydrogen | | 343 | 16 | | | | | |
| Methane | | 197 | 197 | | | | | |
| Etbylene | | | | | | | 5590 | 56 |
| Propylene | | | | | | | | 16520 |
| Pentenes + | | | | | | | | 150 |
| Total | 20629 | 21169 | 21169 | 20719 | 7306 | 13413 | 19003 | 19003 |

In the second step, the hydroisomerised $C_4$ cut underwent fractionation in a distillation column. This column comprised about 90 plates and operated at a pressure of 0.7 MPa in the reflux drum, to allow the use of cooling water in the overhead condenser. The reflux ratio was adjusted to limit the loss of butene-2 in the distillate to about 3% and to reduce the butene-1 and isobutene contents in the bottom product to 0.3% and 0.7% respectively, to limit to a maximum the formation of by-product pentenes and hexenes in the subsequent metathesis step.

In the third step, the bottom fraction from the distillation step which contained mainly butene-2 was reacted with ethylene (overall composition: stream 7 in Table 1) over a metathesis catalyst constituted by rhenium oxide on gamma alumina (8% by weight of rhenium metal), prepared as described in U.S. Pat. No. 4,795,734. The $C_4$ cut was mixed with ethylene supplied to the inlet to the metathesis reactor and with the recycled ethylene and butene streams. The reactor was a moving bed reactor as described in FR-A-2 608 595, at a temperature of 35° C. and at a pressure of 3.5 MPa, and it was coupled with a regenerator operating at 550° C. at atmospheric pressure. The catalyst was extracted from the bottom of the reactor at regular intervals and transferred to the regenerator from which it was returned to the top of the reactor, transfers being made through buffer traps. At the reactor outlet, unconverted ethylene was fractionated in a first distillation column and recycled. A second distillation column separated the propylene and unconverted $C_4$ hydrocarbons which were also recycled. The composition of the metathesis effluent is shown in Table 1, stream 8.

The overall balance of the transformation was as follows. For 100 parts by weight (pw) of $C_4$ cut leaving the steam cracker, 1.6 pw of hydrogen and 28 pw of ethylene were consumed, and 27 pw of isobutene and 83 pw of propylene were produced. For the steam cracker from which the treated $C_4$ cut issues, this balance represented a low ethylene consumption which resulted in a supplemental high production of propylene without having to modify the operating conditions of the cracker.

The advantage of this process is thus the highly selective production of a polymerisation quality propylene due to metathesis of a butene-2 feed containing only small amounts of butene-1 and isobutene, the feed having been obtained by isomerisation and fractionation of a $C_4$ cut.

What is claimed is:

1. A facility for converting an olefinic $C_4$ cut to isobutene and propylene comprising, in succession:
   1) a zone I for selective hydrogenation of olefins in the olefinic C4 cut with simultaneous isomerisation of butene-1 to butene-2, said zone comprising at least one means for introducing the olefinic C4 cut to be converted, at least one outlet means for removing an effluent, and at least one means for introducing hydrogen, said zone also comprising at least one catalyst bed;
   2) a separation zone II, comprising at least one inlet means for introducing the effluent from zone I directly connected to said at least one outlet means for removing the effluent from zone I, at least one means for removing a first fraction comprising isobutene and butene-1, and at least one means for removing a second fraction comprising butene-2 and n-butane, wherein the second fraction comprises at most 1% by weight of isobutene and at most 1% by weight of butene-1;
   3) a metathesis zone III for metathesis of butene-2 with ethylene to produce propylene, wherein the metathesis zone comprises at least one means for introducing butene-2 from the second fraction of the separation zone, at least one means for introducing ethylene, and at least one means for removing propylene, and at least one catalyst comprising at least one rhenium oxide deposited on a support.

2. A facility according to claim 1, characterized in that the metathesis zone contains a moving bed catalyst.

3. A facility according to claim 1, characterized in that the catalyst bed of zone I comprises at least one metal selected from the group consisting of nickel, palladium and platinum, deposited on a support.

4. A facility according to claim 1, characterized in that the means for introducing the C4 cut to be converted is connected to a steam cracking zone, and in that the means for introducing ethylene into the metathesis zone is connected to the steam cracking zone.

5. A facility according to claim 1, wherein the catalyst of the metathesis zone further comprises niobium oxide or tantalum oxide deposited on the support,
   wherein 0.01% to 30% by weight of the catalyst is niobium metal or tantalum metal, and
   wherein 0.01% to 20% by weight of the catalyst is metallic rhenium, and
   wherein at least 75% by weight of the support of the catalyst is alumina.

\* \* \* \* \*